United States Patent [19]

Reichmann et al.

[11] 4,340,712

[45] Jul. 20, 1982

[54] PROCESS FOR THE PREPARATION OF POLYISOCYANATES CONTAINING BIURET AND/OR HIGHER POLYURET GROUPS AND USE THEREOF AS SYNTHESIS COMPONENT IN THE PREPARATION OF POLYURETHANE PLASTICS

[75] Inventors: Wolfgang Reichmann, Duesseldorf; Klaus König; Manfred Schönfelder, both of Leverkusen, all of Fed. Rep. of Germany

[73] Assignee: Bayer Aktiengesellschaft, Leverkusen, Fed. Rep. of Germany

[21] Appl. No.: 105,368

[22] Filed: Dec. 19, 1979

[30] Foreign Application Priority Data

Dec. 30, 1978 [DE] Fed. Rep. of Germany ....... 2856826

[51] Int. Cl.³ .................... C08G 18/78; C07C 127/22
[52] U.S. Cl. ............................... 528/45; 260/453 AB; 521/160; 528/59; 544/388; 548/341; 560/125; 560/169
[58] Field of Search ................ 260/453 AB; 544/388; 548/341; 528/45, 59

[56] References Cited

U.S. PATENT DOCUMENTS

| | | | |
|---|---|---|---|
| 3,124,605 | 3/1964 | Wagner | 260/453 AB |
| 3,358,010 | 12/1967 | Britain | 260/453 AB |
| 3,862,973 | 1/1975 | Dietrich et al. | 260/453 AB |
| 3,903,126 | 9/1975 | Woerner et al. | 260/453 AB |
| 3,903,127 | 9/1975 | Wagner et al. | 260/453 AB |
| 4,051,165 | 9/1977 | Wagner et al. | 260/453 AB |
| 4,147,714 | 4/1979 | Hetzel et al. | 260/453 AB |
| 4,220,749 | 9/1980 | Reichmann | 260/453 AB |

FOREIGN PATENT DOCUMENTS

| | | |
|---|---|---|
| 744750 | 10/1966 | Canada . |
| 1101394 | 3/1961 | Fed. Rep. of Germany . |
| 1043672 | 9/1966 | United Kingdom . |
| 1043673 | 9/1966 | United Kingdom . |

*Primary Examiner*—Dolph H. Torrence
*Attorney, Agent, or Firm*—Gene Harsh; Lawrence S. Pope; Thomas W. Roy

[57] ABSTRACT

A process for the preparation of polyisocyanates containing biuret and/or higher polyuret groups by reacting secondary diamines with diisocyanates characterized in that the reaction is carried out in the presence of catalytic quantities of strong acids which form mixed carbamic acid anhydrides with isocyanates. Alternatively, the secondary diamines may be reacted with organic diisocyanates in the absence of catalysts to form a urea diisocyanate which is then reacted in the presence of catalytic quantities of strong acids which form mixed carbamic acid anhydrides either with the same diisocyanate used in the first step or a second diisocyanate. The invention also relates to the polyisocyanates containing biuret and/or higher polyuret groups obtainable by this process.

3 Claims, No Drawings

PROCESS FOR THE PREPARATION OF POLYISOCYANATES CONTAINING BIURET AND/OR HIGHER POLYURET GROUPS AND USE THEREOF AS SYNTHESIS COMPONENT IN THE PREPARATION OF POLYURETHANE PLASTICS

FIELD OF THE INVENTION

This invention relates to a new process for the preparation of polyisocyanates containing biuret and/or polyuret groups, to the polyisocyanates obtainable by this process and to the use of these polyisocyanates as isocyanate component in the preparation of polyurethane plastics.

BACKGROUND OF THE INVENTION

Polyisocyanates containing biuret groups are known and are used as starting materials for high-grade, light-stable lacquers. They may be obtained, for example, from diisocyanates and water (German Auslegeschrift No. 1,101,394 or U.S. Pat. No. 3,124,605), hydrogen sulphide (German Auslegeschrift No. 1,165,580), formic acid (German Auslegeschrift No. 1,174,760), tertiary alcohols (German Auslegeschrift Nos. 1,543,178 and 1,931,055 or U.S. Pat. No. 3,358,010) or monoamines (German Offenlegungsschrift No. 2,308,015 and U.S. Pat. No. 3,903,127).

In this conventional process, amino groups are initially formed from some of the isocyanate groups and then further react with excess diisocyanate, via the corresponding urea diisocyanates, to form biuret polyisocyanates. The conversion of the isocyanate groups into amino groups is always accompanied by the formation of gaseous secondary products, such as carbon dioxide, carbon monoxide, carbon sulphoxide or olefins, whose elimination may give rise to emission problems. In the heterogeneous reaction of diisocyanates with water, an additional problem lies in the formation of insoluble polyureas which are difficult to separate off. However, a particular disadvantage of these known processes is that some of the isocyanate groups in the diisocyanates, used as starting material, are initially destroyed through the formation of amino groups.

Accordingly, there has also been no shortage of attempts to produce polyisocyanates containing biuret groups by directly reacting diamines with diisocyanates without any elimination of volatile secondary products and without the destruction of isocyanate groups for amine formation.

Due to the high reactivity of aliphatic amino groups to isocyanate groups, considerable practical difficulties were encountered. The most difficult is the reaction of primary diamines with diisocyanates because of the great tendency for insoluble polyureas and cross-linked products to be formed.

As may be seen from German Offenlegungsschrift No. 2,261,065, for example, uneconomically long after-heating at elevated temperature is required for completing the reaction where readily available starting materials, such as hexamethylene diamine and hexamethylene diisocyanate, are used. This greatly impairs the properties of the end products, particularly their natural color. According to German Offenlegungsschrift No. 2,609,995 and U.S. Pat. No. 4,147,714, these disadvantages may be obviated by introducing the diamine into the diisocyanate in vapor form under carefully controlled conditions. In this process, however, steps have to be taken to ensure that no diisocyanate enters the feed pipe because otherwise blockages attributable to urea formation may rapidly occur.

In these conventional processes, formation of the biuret polyisocyanates is accompanied by rearrangement reactions by which the diamine used is converted into the corresponding diisocyanate depending upon the NCO/NH$_2$-ratio. As a result, mixtures of different diisocyanates accumulate as distillates during separation of the unreacted diisocyanate from the biuret polyisocyanate unless diamines and diisocyanates of the same constitution are used. Another disadvantage is that more or less large quantities of the diisocyanate formed from the diamine by trans-biuretization remain behind as a monomer component in the biuret polyisocyanate itself.

According to German Offenlegungsschrift No. 2,010,887 and U.S. Pat. No. 3,862,973, the direct reaction of secondary diamines may be carried out with diisocyanates. By this process, it is possible to produce primarily biuret polyisocyanates containing aromatically bound isocyanate groups which, unfortunately, are not suitable for high-quality light-stable lacquers. Where aliphatic diamines are used in combination with aliphatic diisocyanates, the corresponding bis-urea diisocyanates are spontaneously formed in this known process, but unfortunately cannot be readily reacted with more diisocyanate to form higher biuret polyisocyanates.

An object of the present invention is to provide a new process by which it is readily possible to produce high-quality, modified aliphatic polyisocyanates which combine the advantages of known biuret polyisocyanates without the process being attended by the above-mentioned disadvantages of the conventional processes.

This object is achieved by the process according to the present invention as described in the following.

SUMMARY OF THE INVENTION

The present invention relates to a process for the preparation of polyisocyanates containing biuret and/or higher polyuret groups by reacting secondary diamines corresponding to the formula:

$$R_1-NH-R_2-NH-R_3$$

with excess quantities of organic diisocyanates corresponding to the formula:

$$R_4(NCO)_2$$

wherein
  R$_1$ and R$_3$, which may be the same or different, each represents an aliphatic hydrocarbon radical containing from 1 to 20 carbon atoms which may also be attached to one another with incorporation of the basic diamine skeleton to form a 5- or 6-membered ring, or a cycloaliphatic hydrocarbon radical containing from 4 to 15 carbon atoms; and
  R$_2$ and R$_4$, which may be the same or different, each represents an aliphatic hydrocarbon radical having a total of from 2 to 20 carbon atoms optionally containing ester groups or a cycloaliphatic hydrocarbon radical containing from 4 to 15 carbon atoms, at least two carbon atoms being arranged between the two nitrogen atoms;

characterized in that the reaction is carried out in the presence of catalytic quantities of strong acids which form mixed carbamic acid anhydrides with isocyanates.

The present invention also relates to a variant of this process which is characterized in that, in a first reaction step, the diamines and diisocyanates used in the above-mentioned process are initially reacted in the absence of a catalyst to form a urea diisocyanate corresponding to the formula:

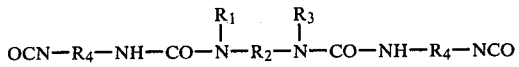

after which the thus-obtained urea diisocyanate is reacted in the presence of the above-mentioned catalysts either with more diisocyanate corresponding to the formula:

or with another diisocyanate corresponding to the formula:

wherein $R_1$, $R_2$, $R_3$, and $R_4$ are as defined above and $R_5$ corresponds to the definition of $R_4$, but is not the same as $R_4$.

The present invention also relates to the polyisocyanates containing biuret and/or higher polyuret groups obtainable by this process.

Furthermore, the present invention also relates to the use of the polyisocyanates containing biuret and/or higher polyuret groups obtainable by this process, optionally blocked with blocking agents for isocyanate groups, as synthesis component in the preparation of polyurethane plastics by the isocyanate polyaddition process.

DETAILED DESCRIPTION OF THE INVENTION

In the above formulae and also in the following, the radicals $R_1$, $R_2$, $R_3$, $R_4$, and $R_5$ are as defined above. These radicals preferably have the following meanings:

$R_1$ and $R_3$, which may be the same or different, each preferably represents an aliphatic hydrocarbon radical containing from 1 to 3 carbon atoms;

$R_2$ preferably represents an aliphatic hydrocarbon radical containing from 2 to 6 carbon atoms or a cycloaliphatic hydrocarbon radical containing from 6 to 10 carbon atoms;

$R_4$ and $R_5$, represent different hydrocarbon radicals and preferably represent aliphatic hydrocarbon radicals containing from 6 to 10 carbon atoms or cycloaliphatic hydrocarbon radicals containing from 6 to 10 carbon atoms.

$R_4$ represents in particular a hexamethylene radical.

Starting materials for the process according to the present invention are diamines corresponding to the formula:

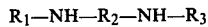

and diisocyanates corresponding to the formula:

and optionally to the formula:

Examples of suitable diamines corresponding to the above formula are N,N'-dimethyl ethylene diamine, N,N'-diethyl ethylene diamine, N,N'-diisopropyl ethylene diamine, N,N'-diisopropyl trimethylene diamine, N,N'-diisopropyl hexamethylene diamine, N-methyl-N'-decyl hexamethylene diamine, N-cyclohexyl-N'-stearyl ethylene diamine,2,6-bis-(methylamino)-1-hexane carboxylic acid ethyl ester or 1,4-piperazine. It is also possible to use mixtures of the diamines exemplified above.

Diisocyanates which may be used in the process according to the present invention are, for example, tetramethylene diisocyanate, hexamethylene, diisocyanate, 2,4,4-trimethyl hexamethylene diisocyanate, undecamethylene diisocyanate, 1-isocyanato-3-isocyanatomethyl-3,5,5-trimethyl cyclohexane (isophorone diisocyanate), 1,4-diisocyanatocyclohexane, 4,4'-diisocyanatodicyclohexyl methane, 1,2-bis-(isocyanatomethyl)-cyclobutane or 6-isocyanato-2-caproic acid isocyanatoethyl ester.

While the reaction of primary or secondary diamines with diisocyanates to form the corresponding ureas or biurets belongs to the prior art, there has been no process which, when a secondary diamine is used, enables the addition reaction between amine and isocyanate to progress beyond the biuret stage. This is due to the lack of reactivity of biurets with respect to aliphatic diisocyanates which may only be overcome by using suitable catalysts. In the presence of the catalysts used in accordance with the present invention, the biuret polyisocyanates may readily be further reacted to form polyisocyanates containing higher polyuret groups. In addition, the presence of the catalysts according to the present invention also facilitates the very sluggish reaction of the urea diisocyanates initially formed with more diisocyanate eliminating the need for the reactants to be subjected to prolonged heating to high temperatures.

The catalysts used in accordance with the present invention are strong proton-releasing acids which react with isocyanates, particularly aliphatic or cycloaliphatic isocyanates, to form a mixed acid anhydride. The carbamic acid corresponding to the isocyanate and the proton-releasing acid representing the acids of the mixed acid anhydride. Thus, such acids HX (X=acid residue after release of the proton), which are suitable for the process according to the present invention, react with isocyanates Y—NCO to form adducts of the formula: Y—NH—CO—X which may be regarded as a mixed anhydride of the carbamic acid Y—NH—COOH and the acid HX.

Examples of suitable acids are hydrogen halides, such as hydrogen fluoride, hydrogen chloride, hydrogen bromide or hydrogen iodide, chlorosulphonic acid, fluorosulphonic acid, sulphuric acid, alkane sulphonic acids, such as methane sulphonic acid, or perhalogenated alkane sulphonic acids, such as trifluoromethane sulphonic acid. Hydrogen chloride is the acid preferably used in the process according to the present invention. Instead of using the acids, it is, of course, possible in the process according to the present invention to use both ammonium salts corresponding to the acids with the amines used as starting material or the mixed carbamic acid anhydrides corresponding to the acids, particularly carbamic acid chlorides, of the diisocyanates used as starting material or of other isocyanates. In general, the catalysts are used in quantities of from about 0.001 to 10%, by weight, preferably from about 0.01 to 1.0%, by weight, based on the total weight of the reactants.

The process according to the present invention is generally carried out at temperatures of from about 0° to 140° C., preferably from about 50° to 90° C., the further reaction beyond the urea diisocyanate stage to form polyisocyanates containing biuret and higher polyuret groups generally taking place at temperatures of from about 90° to 140° C. The acid catalysts according to the present invention, exemplified above, enable isocyanate addition products containing biuret and polyuret groups to be obtained under mild reaction conditions from aliphatic diisocyanates and aliphatic secondary diamines.

There are essentially two variants to the process according to the present invention:

In the first embodiment of the instant process, the catalyst is actually added at the beginning of the reaction. To this end, the catalyst may be initially introduced, for example, with the diisocyanate or may be introduced with the amines in the form of its ammonium salt. Accordingly, the diisocyanate and the diamine are reacted in the presence of the catalyst from the outset in this first embodiment of the instant process. To this end, the diisocyanate is preferably introduced at a temperature of from about 0° to 100° C., the diamine then being added to the diisocyanate. The quantitative ratios between the reactants are selected in such a way that an NCO/NH-equivalent ratio of from about 4:1 to 30:1 is present in the reaction mixture. The corresponding urea diisocyanates are spontaneously formed. The further reaction to form the end product containing biuret and/or polyuret groups generally takes place thereafter by straightforward heating to a temperature of from about 90° to 140° C. The course of the reaction may be followed by monitoring the reduction in the isocyanate content. In this way, the reaction may be terminated simply by cooling to room temperature. Where volatile catalysts are used, the reaction may be carried out under pressure in order to avoid losses of catalyst which may occur at elevated temperatures under normal pressure. The necessary reaction times are dependent upon the nature of the starting products, upon the temperature and, in particular, upon the type and quantity of catalyst used. In general, the reaction times amount to between about 1 and 20 hours, preferably between about 2 and 8 hours. Clear, colorless to pale yellowish reaction solutions are obtained upon completion of the reaction. This is attributable, in particular, to the relatively low reaction temperature.

In a second embodiment of the instant process, a urea diisocyanate corresponding to the formula:

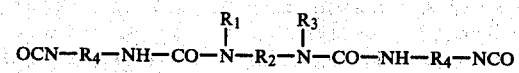

where $R_1$, $R_2$, $R_3$, and $R_4$ are as defined above; is initially formed from a diamine and a diisocyanate of the type exemplified in the absence of a catalyst. In this embodiment, too, the reactants are used in quantities corresponding to an NCO/NH-equivalent ratio of from about 4:1 to 30:1. The reaction temperature is generally between about 0° and 100° C., preferably between about 50° and 90° C. After formation of the urea, which takes place spontaneously even in the absence of the catalyst, formation of the biuret and/or polyuret is initiated as described above in a second reaction stage after addition of the catalyst and preferably with an increase in the reaction temperature to from about 90° to 140° C. However, the biurets and higher polyurets may also be formed by removing the excess diisocyanate corresponding to the formula:

wherein $R_4$ is defined as above, which is still present in admixture with the urea diisocyanate, for example by distillation, and replacing it by another diisocyanate corresponding to the formula:

wherein $R_5$ is defined as above, before formation of the biuret or polyuret structures by the addition of the catalyst and the above-mentioned increase in temperature.

In this two-stage embodiment of the instant process, steps are preferably taken to ensure that the urea diisocyanate and the diisocyanate further reacting therewith to form the biuret or polyuret are present in quantities which correspond to an NCO/NH-equivalent ratio of from about 2:1 to 30:1. The course of the reaction is monitored and the reaction terminated in the same way as described with reference to the first embodiment.

In both embodiments of the instant process, the reaction is generally terminated at a time when on average, based on one mol of amino groups in the diamine, a total of from about 2 to 2.5 mols of NCO-groups have been consumed. However, it is also possible to obtain a higher "degree of polyuretization", i.e., to react three and more NCO-groups of the diisocyanate per mol of amino groups. In this case, the viscosities of the products rapidly increase.

The catalyst is generally removed by distilling the reaction mixture in vacuo. Where the catalyst used is a hydrogen halide, it may alternatively be removed, particularly where it is used in small quantities, by the addition of equimolar quantities of propylene oxide. It is also possible to remove the catalyst, for example, by thin-layer evaporation providing the crude isocyanate is freed from excess diisocyanate. The thin-layer distillate, which in addition to the diisocyanate contains the catalyst, may be reused as starting material.

In cases where it is intended to remove excess diisocyanate, this is generally done by thin-layer evaporation. However, excess diisocyanate may also be removed by extraction using suitable solvents, such as hexane, heptane, etc.

The crude isocyanates may be used as such. In most cases, however, they are preferably separated from monomeric isocyanate components by thin-layer evaporation or by extraction. The monomer-free products are light yellow oils or even solid resins; the NCO-content amounts to between about 5 and 22%, by weight.

The process is particularly suitable for continuous working. In such cases, it is possible, for example, to arrange several reaction vessels one behind the other in the form of a cascade. In the first reaction vessel, the starting products, i.e., the diisocyanate and the diamine or the urea diisocyanate produced beforehand are mixed at about 80° C. and the catalyst subsequently added. The catalyst may even be added to the second reaction vessel at a temperature of from about 90° to 140° C. The further reaction by which the polyuret polyisocyanate is obtained takes place in the third reaction vessel and in further reaction vessels, if any, at a temperature of from about 90° to 140° C., the required "degree of polyuretization" being adjusted by controlling the temperature and the residence time. Excess diisocyanate and the catalyst are removed, for example, through a tubular-coil evaporator combined with a following thin-layer evaporator. The distillates consisting of diisocyanate and catalyst are combined and returned to the process. It is also possible to separate the catalyst from the diisocyanate before returning them to the start of the process. The polyisocyanate is obtained as the thin-layer distillation residue.

In the working of the instant process, the properties of the modified polyisocyanates obtained, particularly the NCO-functionality and the NCO-content thereof, and also the viscosity thereof may be controlled by (a) the choice of suitable starting materials, and/or (b) particularly easily, by adjusting the "degree of polyuretization", i.e., the number of NCO-groups reacted per amino group.

The main advantage of the instant process over the conventional processes according to German Offenlegungsschrift Nos. 2,261,065 or 2,609,995 and U.S. Pat. No. 4,147,714 lies in the fact that virtually no polyurea, difficulty soluble in excess diisocyanate, is formed so that no complicated measures have to be taken to prevent its formation. By virtue of the instant process, it is possible to produce the high-quality lacquer-grade polyisocyanates without the need to apply extremely high temperatures, i.e., temperatures above 140° C., so that substantially colorless products having a very low content of undesirable secondary products of fairly high molecular weight are always obtained.

The end products obtained by the instant process may be used, in particular, as the isocyanate component in the preparation of polyurethane plastics by the isocyanate polyaddition process. They are suitable both for the production of polyurethane foams and also for the production of elastomers, coatings or adhesives. Where the end products obtained by the instant process are used for the first of these applications, there is often no need for the excess diisocyanate to be distilled off on completion of the reaction. The monomer-free end products obtained by the instant process are excellent starting materials for the production of high-quality weatherproof and light-stable lacquers.

Where the end products obtained by the instant process are used as "lacquer-grade isocyanates", their outstanding compatibility with conventional commercial-grade polyhydroxy polyacrylates is a particular advantage. Another advantage of the instant products over known biuret polyisocyanates lies in the fact that they are stable with respect to resplitting of the monomers. In other words, the monomer content of the instant polyisocyanates does not increase even during storage at elevated temperature (50° C.). The end products obtained by the instant process may also be used in blocked form, i.e., blocked with blocking agents for isocyanate groups, for the production of two-component polyurethane lacquers. The known blocking agents, such as ε-caprolactam, malonic acid dimethyl ester or acetoacetic acid ethyl ester, may be used for this purpose. The end products obtained by the instant process are converted into the corresponding blocked polyisocyanates by long-established conventional processes.

The following Examples serve to illustrate the process of the instant invention without restricting it in any way. In the Examples, all quantities quoted represent percent by weight or parts by weight unless otherwise indicated.

EXAMPLE 1

In a 4-liter four-necked flask equipped with a stirrer, reflux condenser and contact thermometer, 200 g (1 mol) of 1,6-diisopropylaminohexane were added dropwise over a period of 1 hour at from 80° to 90° C. to 3696 g (22 mols) of 1,6-diisocyanatohexane. After the amine had been added, the NCO-content of the clear reaction mixture amounted to 45.3%. This corresponds to a total conversion of 2 NCO-groups, i.e., the corresponding urea diisocyanate had formed. 4 g of hydrogen chloride were then added to the solution and the reaction temperature was increased to from 100° to 110° C. After 3 hours, the NCO-content of the solution had fallen to 43.2% (corresponding to a consumption of 4 NCO-groups per mol of diamine). The reaction solution was cooled to room temperature. Subsequent thin-layer distillation gave 750 g of a polyisocyanate having an NCO-content of 17.8% and a viscosity of 130,000 mPa.s at 20° C. (residual content of monomeric 1,6-diisocyanatohexane=0.51%).

EXAMPLE 2

In a manner similar to Group 1, 172 g (1 mol) of 1,4-diisopropylaminobutane were added dropwise over a period of 20 minutes at from 70° to 80° C. to 3696 g (22 mols) of 1,6-diisocyanatohexane. The NCO-content of the clear reaction solution amounted to 45.6% (corresponding to a consumption of 2 NCO-groups). The reaction temperature was then increased to from 100° to 110° C. and 4 g of hydrogen chloride added to the mixture. After 2 hours, the NCO-content of the solution had fallen to a 43.4% (corresponding to a consumption of 4 NCO-groups per mol of diamine). The reaction solution was worked-up in the same way as described in Example 1, giving 730 g of a polyisocyanate having an NCO-content of 18.5% and a viscosity of 146,000 mPa.s at 20° C. The residual monomer content amounted to 0.64%.

EXAMPLE 3

In a manner similar to Example 1, 172 g (1 mol) of 1,4-diisopropylaminobutane were added dropwise over a period of 20 minutes at from 70° to 80° C. to 4032 g (24 mols) of 1,6-diisocyanatohexane containing 4 g of hydrogen chloride accommodated in a 6-liter four-necked flask. After the amine had been added, the reaction temperature of the clear solution was increased to 100° C. After stirring for 8 hours at that temperature, the NCO-content of the mixture amounted to 41.8% (corresponding to a consumption of 6.1 NCO-groups per mol of diamine). Thin-layer distillation gave 1056 g of a polyisocyanate having an NCO-content of 20.1% and a viscosity of 24,000 mPa.s at 20° C. (monomer content 0.49%).

EXAMPLE 4

In a manner similar to Example 1, 200 g (1 mol) of 1,6-diisopropylamino hexane were added dropwise over a period of 30 minutes at from 90° to 100° C. to 4032 g (24 mols) of 1,6-diisocyanatohexane containing 4 g of hydrogen chloride accommodated in a 6-liter flask. After 8 hours at from 110° to 115° C., the NCO-content of the clear reaction solution amounted to 42.5% (corresponding to a consumption of 5.2 NCO-groups per mol of diamine). Working-up produced 900 g of a polyisocyanate having an NCO-content of 18.7% and a viscosity of 26,100 mPa.s at 20° C. (monomer content 0.35%).

What is claimed is:

1. A process for the preparation of polyisocyanates containing biuret and/or higher polyuret groups comprising reacting secondary diamines corresponding to the formula:

$$R_1-NH-R_2-NH-R_3$$

with excess quantities of organic diisocyanates corresponding to the formula:

$$R_4(NCO)_2$$

wherein
  $R_1$ and $R_3$, which may be the same or different, each represents an aliphatic hydrocarbon radical containing from 1 to 20 carbon atoms which may also be attached to one another with incorporation of the basic diamine skeleton to form a 5- or 6-membered ring, or a cycloaliphatic hydrocarbon radical containing from 4 to 15 carbon atoms; and
  $R_2$ and $R_4$, which may be the same or different, each represents an aliphatic hydrocarbon radical having a total of from 2 to 20 carbon atoms optionally containing ester groups or a cycloaliphatic hydrocarbon radical containing from 4 to 15 carbon atoms, at least 2 carbon atoms being arranged between the two nitrogen atoms;
characterized in that
  (a) the reaction is carried out in the presence of catalytic quantities of strong acids which form mixed carbamic acid anhydrides with isocyanates, and
  (b) the reaction product is clear and contains virtually no difficultly soluble polyurea.

2. A process for the preparation of clear polyisocyanates containing biuret and/or higher polyuret groups, but containing virtually no difficultly soluble polyureas comprising reacting secondary diamines corresponding to the formula:

$$R_1-NH-R_2-NH-R_3$$

with excess quantities of organic diisocyanates corresponding to the formula:

$$R_4(NCO)_2$$

wherein
  $R_1$ and $R_3$, which may be the same or different, each represents an aliphatic hydrocarbon radical containing from 1 to 20 carbon atoms which may also be attached to one another with incorporation of the basic diamine skeleton to form a 5- or 6-membered ring, or a cycloaliphatic hydrocarbon radical containing from 4 to 15 carbon atoms; and
  $R_2$ and $R_4$, which may be the same or different, each represents an aliphatic hydrocarbon radical having a total of from 2 to 20 carbon atoms optionally containing ester groups or a cycloaliphatic hydrocarbon radical containing from 4 to 15 carbon atoms, at least 2 carbon atoms being arranged between the two nitrogen atoms;
characterized in that the reaction is carried out in the absence of catalysts to form urea diisocyanate corresponding to the formula:

$$OCN-R_4-NH-CO-\underset{\underset{R_1}{|}}{N}-R_2-\underset{\underset{R_3}{|}}{N}-CO-NH-R_4-NCO$$

and subsequently reacting said urea diisocyanates thus formed in the presence of catalytic quantities of strong acids which form mixed carbamic acid anhydrides with isocyanates, with more diisocyanate corresponding to the formula:

$$R_4(NCO)_2$$

or with another diisocyanate corresponding to the formula:

$$R_5(NCO)_2$$

wherein
  $R_5$ corresponds to the definition of $R_4$ but is not the same as $R_4$.

3. A process for producing polyurethane by reacting a polyisocyanate with active hydrogen containing material, wherein said polyisocyanate is the polyisocyanate as produced by the process of claims 1 or 2, optionally blocked with blocking agents for isocyanate groups.

* * * * *